(12) United States Patent
Sugita et al.

(10) Patent No.: US 7,687,621 B2
(45) Date of Patent: Mar. 30, 2010

(54) PROCESS FOR REGENERATING CATALYST FOR PRODUCING E-CAPROLACTAM AND PROCESS FOR PRODUCING E-CAPROLACTAM

(75) Inventors: Keisuke Sugita, Kyoto (JP); Masaru Kitamura, Niihama (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 229 days.

(21) Appl. No.: 11/822,141

(22) Filed: Jul. 2, 2007

(65) Prior Publication Data
US 2008/0033168 A1 Feb. 7, 2008

(30) Foreign Application Priority Data
Jul. 4, 2006 (JP) ............................. 2006-184250

(51) Int. Cl.
*C07D 201/04* (2006.01)
(52) U.S. Cl. ...................................................... 540/536
(58) Field of Classification Search ................. 540/536
See application file for complete search history.

(56) References Cited

U.S. PATENT DOCUMENTS

| 4,319,983 | A | 3/1982 | Yoo |
| 5,212,302 | A | 5/1993 | Kitamura et al. |
| 6,303,099 | B1 | 10/2001 | Ichihashi et al. |
| 7,026,474 | B2 | 4/2006 | Sugita et al. |

FOREIGN PATENT DOCUMENTS

| EP | 0 494 535 A1 | 7/1992 |
| EP | 1 065 167 A1 | 1/2001 |
| EP | 1 593 433 A1 | 11/2005 |
| JP | 2-250866 | 10/1990 |
| JP | 2-275850 | 11/1990 |
| JP | 3-207454 | 9/1991 |
| JP | 5-9180 | 1/1993 |
| JP | 5-201965 | 8/1993 |
| JP | 5-201966 | 8/1993 |
| JP | 6-107627 | 4/1994 |
| JP | 2003-320260 | 11/2003 |
| JP | 2005-224752 | 8/2005 |

*Primary Examiner*—Bruck Kifle
(74) *Attorney, Agent, or Firm*—Foley & Lardner LLP

(57) ABSTRACT

The present invention provides a process for regenerating a catalyst for producing e-caprolactam comprising the steps of adsorbing a silicon compound on a zeolite catalyst that had been used for a Beckmann rearrangement reaction of cyclohexanone oxime and contacting the catalyst with an aqueous solution containing a compound selected from a quaternary ammonium compound, lower alkylamines and ammonia. The present invention also provides a process for producing e-caprolactam comprising subjecting cyclohexanone oxime to the Beckmann rearrangement reaction in the presence of the catalyst thus regenerated.

5 Claims, No Drawings

PROCESS FOR REGENERATING CATALYST FOR PRODUCING E-CAPROLACTAM AND PROCESS FOR PRODUCING E-CAPROLACTAM

BACKGROUND OF THE INVENTION

1. Field of the Invention

The present invention relates to a process for regenerating a catalyst that had been used for a Beckmann rearrangement reaction of cyclohexanone oxime to produce e-caprolactam. The present invention also relates to a process for producing e-caprolactam by subjecting cyclohexanone oxime to the Beckmann rearrangement reaction with the use of the catalyst thus regenerated.

2. Description of the Related Art

A process for subjecting cyclohexanone oxime to Beckmann rearrangement reaction in the presence of a zeolite catalyst is known as one of processes for producing e-caprolactam. The activity and selectivity of this catalyst usually deteriorate as the time of its use passes away to cause deterioration of the conversion of cyclohexanone oxime and the selectivity to e-caprolactam; therefore, it is proposed as a regenerating process thereof, for example, in JP-5-9180-A (corresponding to EP 0494535 A1) that the used catalyst is contacted with ammonia. Also, it is proposed in JP-2003-320260-A (corresponding to EP 1352902 A1) that the used catalyst is contacted with an aqueous solution containing a quaternary ammonium compound and/or lower alkylamines and ammonia. In addition, it is proposed in JP-2005-224752-A (corresponding to EP 1593433 A1) that the used catalyst is contacted with gas containing ammonia and/or amine, carboxylic acid and water.

BRIEF SUMMARY OF THE INVENTION

It is an object of the present invention to provide a further excellent process for regenerating the used catalyst for producing e-caprolactam.

The present invention provides a process for regenerating a catalyst for producing e-caprolactam comprising the steps of adsorbing a silicon compound on a zeolite catalyst that had been used for a Beckmann rearrangement reaction of cyclohexanone oxime and contacting the catalyst with an aqueous solution containing a compound selected from a quaternary ammonium compound, lower alkylamines and ammonia. The present invention also provides a process for producing e-caprolactam comprising subjecting cyclohexanone oxime to the Beckmann rearrangement reaction in the presence of the catalyst thus regenerated.

The present invention has activity and selectivity of a zeolite catalyst that had been used for Beckmann rearrangement reaction of cyclohexanone oxime being effectively recovered, and such regeneration and reuse of the catalyst allows e-caprolactam to be produced over with a favorable yield for a long period.

DESCRIPTION OF THE PREFERRED EMBODIMENTS

A catalyst intended for regeneration by the present invention is a zeolite catalyst used for a Beckmann rearrangement reaction of cyclohexanone oxime. The original zeolite catalyst may substantially contain zeolite only, or contain zeolite and other components. It may be, for example, such that zeolite only is substantially molded, zeolite is mixed with a binder and a reinforcing material and molded, or zeolite is supported on a carrier. The particle diameter thereof is typically 5 mm or less, preferably 3 mm or less.

The zeolite may be crystalline silica in which the skeleton thereof is substantially composed of silicon and oxygen only, or crystalline metallosilicate further containing other elements as an element constituting the skeleton. In the case of crystalline metallosilicate, examples of the elements contained except for silicon and oxygen include Be, B, Al, Ti, V, Cr, Fe, Co, Ni, Cu, Zn, Ga, Ge, Zr, Nb, Sb, La, Hf and Bi; two kinds or more thereof may be contained as required. The atomic ratio of silicon to these elements is preferably 5 or more, more preferably 500 or more.

The zeolite is preferably pentasil zeolite, above all, preferably MFI-type zeolite. The primary particle diameter thereof is preferably 5 µm or less, more preferably 1 µm or less.

The zeolite can be appropriately prepared, for example, in such a manner that a silicon compound is mixed with a quaternary ammonium compound, water and, as required, a metallic compound and subjected to a hydrothermal synthetic reaction, and then the obtained crystal is fired and thereafter further subjected to a contact treatment with ammonia or an ammonium salt.

A Beckmann rearrangement reaction of cyclohexanone oxime with the use of the above-mentioned zeolite catalyst can be appropriately performed under the gaseous phase conditions in fixed bed or fluidized bed, and reaction temperature is typically 250 to 500° C., preferably 300 to 450° C., and reaction pressure is typically 0.005 to 0.5 MPa, preferably 0.005 to 0.2 MPa. The supply rate of cyclohexanone oxime as a material is typically 0.1 to 20 $h^{-1}$, preferably 0.2 to 10 $h^{-1}$ in terms of supply rate per 1 kg of the catalyst (kg/h), namely, space velocity WHSV ($h^{-1}$).

The cyclohexanone oxime may be supplied singly to the reaction system, or together with inert gases such as nitrogen, argon and carbon dioxide to the reaction system. The following are also effective: a process of coexisting with an ether compound as described in JP-2-250866-A (corresponding to EP 0380364 A2), a process of coexisting with lower alcohol as described in JP-2-275850-A (also corresponding to EP 0380364 A2), a process of coexisting with alcohol and/or an ether compound and water as described in JP-5-201965-A (corresponding to EP 0544530 A1), a process of coexisting with ammonia as described in JP-5-201966-A (corresponding to EP 0544531 A1), and a process of coexisting with methylamines as described in JP-6-107627-A.

Cyclohexanone oxime may be prepared, for example, by oximizing cyclohexanone with hydroxylamine or salts thereof, or prepared by ammoximizing cyclohexanone with ammonia and hydrogen peroxide in the presence of a catalyst such as titanosilicate.

The above-mentioned Beckmann rearrangement reaction may be performed in combination with the operation of firing the zeolite catalyst under an oxygen-containing gas atmosphere such as air, and the catalyst-firing treatment allows the carbonaceous material precipitated on the catalyst to be burned and removed, so that persistence in conversion of cyclohexanone oxime and selectivity of e-caprolactam can be improved. For example, in the case of performing the reaction in fixed bed, the following formulation is appropriately adopted: a fixed-bed reaction vessel filled with the catalyst is supplied with cyclohexanone oxime to perform the reaction, thereafter the supply is stopped, subsequently the firing while supplying the oxygen-containing gas is performed, and further these reaction and firing are repeated. Meanwhile, in the case of performing the reaction in fluidized bed, the following formulation is appropriately adopted: a fluidized-bed reaction vessel in which the catalyst is fluidized is supplied with cyclohexanone oxime to perform the reaction, and concurrently the catalyst is extracted continuously or intermittently from the reaction vessel, fired in a firing vessel under an oxygen-containing gas atmosphere, and then returned again to the reaction vessel.

As described above, in the case of subjecting cyclohexanone oxime to the Beckmann rearrangement reaction in the presence of the zeolite catalyst, typically, as operating time passes, that is, as the time of use of the catalyst passes, the carbonaceous material is precipitated on the catalyst and the catalyst is subject to thermal degradation, so that the activity and selectivity of the catalyst deteriorate, that is, the conversion of cyclohexanone oxime and the selectivity of e-caprolactam deteriorate. Then, in the present invention, the adsorption treatment with a silicon compound and the contact treatment with an aqueous solution containing at least one compound selected from a quaternary ammonium compound, a lower alkylamine and ammonia are performed for the used catalyst. These adsorption treatment and contact treatment allow activity and selectivity of the used catalyst to be effectively recovered, and allow a regenerated catalyst having activity and selectivity equal to or better than a brand-new catalyst before being used for the above-mentioned Beckmann rearrangement reaction.

Examples of the silicon compound to be used for the adsorption treatment include organic silicon compounds such as tetramethoxysilane, tetraethoxysilane, tetrapropoxysilane, tetrabutoxysilane, 3-aminopropyltriethoxysilane, 3-aminopropyltrimethoxysilane, N-propyltriethoxysilane, silicon acetate (tetraacetoxysilane), silicon 2-ethylhexoate (tetra-2-ethylhexanoyloxysilane), trimethylchlorosilane and triethylchlorosilane, and inorganic silicon compounds such as monosilane, disilane, sodium silicate (water glass) and colloidal silica; two kinds or more thereof can also be used as required. Among them, alkoxysilanes such as tetramethoxysilane, tetraethoxysilane, tetrapropoxysilane and tetrabutoxysilane are preferable.

The used amount of the silicon compounds is typically 0.1 to 100 parts by weight with respect to 100 parts by weight of the used catalyst.

In the case where the aqueous solution to be used for the contact treatment contains a quaternary ammonium compound, examples of the quaternary ammonium compound include hydroxides and halides of quaternary ammonium of various kinds such as tetramethylammonium, tetraethylammonium, n-propyltrimethylammonium, tetra-n-propylammonium, tetra-n-butylammonium, 4,4'-trimethylenebis(dimethylpiperidium), benzyltrimethylammonium, dibenzyldimethylammonium, 1,1'-butylenebis(4-aza-1-azoniabicyclo[2,2,2]octane) and trimethyladamanthylammonium; two kinds or more thereof can also be used as required. Among them, a tetra-n-propylammonium compound is preferable, and tetra-n-propylammonium hydroxide and tetra-n-propylammonium bromide are more preferable.

In the case where the aqueous solution to be used for the contact treatment contains a lower alkylamine, the lower alkylamine may be a monoalkyl amine, a dialkyl amine or a trialkyl amine; two kinds or more thereof can also be used as required. Typically, a compound represented by the following general formula (1) is appropriately used.

$$NR^1R^2R^3 \quad (1)$$

(In the formula, $R^1$, $R^2$ and $R^3$ denote each independently hydrogen atom or an alkyl group having 1 to 4 carbon atoms, and $R^1$, $R^2$ and $R^3$ are not simultaneously hydrogen atom.)

Specific examples of the lower alkylamine represented by the general formula (1) include monomethylamine, monoethylamine, monopropylamine, monobutylamine, dimethylamine, diethylamine, dipropylamine, dibutylamine, trimethylamine, triethylamine, tripropylamine and tributylamine. Among them, tripropylamine is preferable.

The aqueous solution to be used for the contact treatment has a pH of typically 9 or more, preferably 10 to 13. In the aqueous solution, the concentration of the compound selected from a quaternary ammonium compound, a lower alkylamine and ammonia is typically 2 to 30% by weight, preferably 5 to 25% by weight, which is in terms of the total in the case where plural kinds thereof are contained. In the aqueous solution, ammonia is preferably contained, and at least one compound selected from a quaternary ammonium compound and a lower alkylamine is more preferably contained in addition to ammonia. In this case, the content of the quaternary ammonium compound and the lower alkylamine is typically 0.00001 to 0.1 mol, preferably 0.0001 to 0.05 mol with respect to 1 mol of ammonia, which is in terms of the total in the case where plural kinds thereof are contained.

Other components such as an ammonium salt may be contained as required in the aqueous solution. Examples of the ammonium salt include ammonium nitrate, ammonium acetate, ammonium phosphate, ammonium carbonate, ammonium fluoride, ammonium chloride, ammonium bromide and ammonium sulfate; among them, ammonium nitrate and ammonium acetate are preferable. In the case where an ammonium salt is contained in the aqueous solution, the content thereof is typically 0.001 to 1 mol, preferably 0.01 to 0.1 mol with respect to 1 mol of compounds selected from a quaternary ammonium compound, a lower alkylamine and ammonia.

The used amount of the above-mentioned aqueous solution is typically 100 to 5000 parts by weight with respect to 100 parts by weight of the used catalyst.

The order of the adsorption treatment and the contact treatment is optional; the contact treatment may be performed after the adsorption treatment was performed, the adsorption treatment may be performed after the contact treatment was performed, or the adsorption treatment and the contact treatment may simultaneously be performed, and yet it is preferable that the contact treatment may be performed after the adsorption treatment was performed.

In the case of separately performing the adsorption treatment and the contact treatment, the adsorption treatment can appropriately be performed under the liquid phase conditions such that the silicon compound is dissolved as required in an organic solvent such as an alcohol, water or mixed solvent of an organic solvent and water. Specific examples thereof include a process of immersing the used catalyst in the silicon compound or solution thereof to adsorb the silicon compound on the used catalyst and thereafter of filtering out the excessive silicon compound or solution thereof, and a process of immersing the used catalyst in a solution of silicon compound and thereafter of vaporizing the solvent. The temperature of the adsorption treatment is typically 20 to 150° C. The adsorption treatment may be performed with adding a compound selected from the quaternary ammonium compound, the lower alkylamine and ammonia.

In the case of separately performing the adsorption treatment and the contact treatment, the contact treatment may be performed in batch system or continuous system; for example, the used catalyst may be immersed and stirred in the aqueous solution containing a compound selected from a quaternary ammonium compound, a lower alkylamine and ammonia in a stirred vessel, or the aqueous solution may be circulated through a tubular container filled with the used catalyst. The temperature of the contact treatment is typically 50 to 250° C., preferably 50 to 200° C. and more preferably 60 to 150° C., and the time of the contact treatment is typically 0.1 to 10 hours. The used catalyst after the contact treatment is subject to treatments such as washing and drying as required.

In the case of simultaneously performing the adsorption treatment and the contact treatment, the silicon compound or solution thereof is added to the aqueous solution containing a compound selected from a quaternary ammonium compound, a lower alkylamine and ammonia to preferably treat the used catalyst by using this aqueous solution on the same conditions as the contact treatment described above.

The used catalyst that is subjected to the adsorption treatment and the contact treatment may be fired previously under an oxygen-containing gas atmosphere such as air so that the carbonaceous material precipitated on the catalyst may be burned and removed, or may be subjected to the treatments of the present invention without being fired. This firing may be performed in coexistence with an alcohol in accordance with the process proposed in JP-3-207454-A (corresponding to EP 0388070 A1), for example.

The regenerated catalyst obtained in the above manner can be reused for the above-mentioned Beckmann rearrangement reaction of cyclohexanone oxime, and such regeneration and reuse of the catalyst allows e-caprolactam to be produced with high yield for a long period.

As described above, in the case of performing the Beckmann rearrangement reaction in combination with catalyst firing treatment, the catalyst after this firing treatment is preferably subject to the adsorption treatment and the contact treatment. For example, as described above, in the case where the reaction by supply of cyclohexanone oxime and the firing by supply of oxygen-containing gas are repeated in a fixed-bed reaction vessel filled with the catalyst, the catalyst is preferred to be subject to the adsorption treatment and the contact treatment after the firing every time or at several-time intervals, and on this occasion, the catalyst may be subject to the adsorption treatment and the contact treatment while the catalyst remain filled in the reaction vessel, or the catalyst may be extracted once from the reaction vessel, subject to the adsorption treatment and the contact treatment, and thereafter filled again into the reaction vessel. Meanwhile, as described above, in the case where the reaction is performed while circulating the catalyst between a fluidized-bed reaction vessel and a firing vessel, a part of the catalyst is preferred to be extracted from the firing vessel and be subject to the adsorption treatment and the contact treatment, and the catalyst after the treatments may be returned again to the firing vessel or introduced into the reaction vessel.

Known processes can properly be adopted as an after-treatment of the reaction mixture obtained by the above-mentioned Beckmann rearrangement reaction; for example, the reaction product gas is cooled, condensed and thereafter subject to operations such as extraction, distillation and crystallization, so that e-caprolactam can be separated therefrom.

EXAMPLES

Examples of the present invention are hereinafter described and yet the present invention is not limited thereto. The carbon content in a catalyst was assayed using NCH quantitative analyzer (trade name; Sumigraph NCH-21 (based on combustion by circulating oxygen, detected by TCD-GC), manufactured by Sumika Chemical Analysis Service, Ltd.). The Y space velocity WHSV ($h^{-1}$) of cyclohexanone oxime was calculated by dividing the supply rate (g/h) of cyclohexanone oxime by weight (g) of catalyst. The analyses of cyclohexanone oxime and e-caprolactam were performed by gas chromatography, and conversion of cyclohexanone oxime and selectivity of e-caprolactam were each calculated by the following expressions on the conditions that the number of moles of supplied cyclohexanone oxime was X, the number of moles of unreacted cyclohexanone oxime was Y and the number of moles of produced e-caprolactam was Z.

conversion of cyclohexanone oxime (%)=[(X−Y)/X]×100 selectivity of e-caprolactam (%)=[Z/(X−Y)]×100

Reference Example 1

(a) Acquisition of a Used Catalyst

Particles with a particle diameter of 0.3 mm or less having MFI zeolite, a crystalline silica, as the main component, was used as a catalyst to perform reaction at a temperature of 380° C. for 6 months by extracting reaction product gas while supplying a fluidized-bed reaction vessel, in which the catalyst is fluidized, with vaporized cyclohexanone oxime, vaporized methanol and nitrogen gas. In the meantime, the space velocity WHSV of cyclohexanone oxime was determined at 2 $h^{-1}$, the supply percentage of methanol was determined at 1.8 kg with respect to 1 kg of cyclohexanone oxime and the supply percentage of nitrogen gas was determined at 0.8 L with respect to 1 kg of cyclohexanone oxime. Also, in the meantime, a part of the catalyst was extracted from the reaction vessel, introduced into the firing vessel, fired under air ventilation at a temperature of 500° C. and a residence time of 20 hours, and thereafter introduced again into the reaction vessel to thereby circulate the catalyst between the reaction vessel and the firing vessel. A part of the catalyst was extracted from the firing vessel to obtain USED CATALYST A. The carbon content of USED CATALYST A was 0.05% by weight. A part of the catalyst was extracted from the reaction vessel to obtain USED CATALYST B. The carbon content of USED CATALYST B was 1.2% by weight. A part of USED CATALYST B was fired under an atmosphere of air at a temperature of 340° C. for 1 hour to obtain USED CATALYST C. The carbon content of USED CATALYST C was 0.25% by weight.

(b) Evaluation of the Used Catalyst 0.375 g of USED CATALYST A was filled into a reaction tube with an inside diameter of 1 cm, made of quartz glass, to form a catalyst layer, which was subject to a preheat treatment under a nitrogen ventilation of 4.2 L/h at a temperature of 350° C. for 1 hour. Subsequently, under a nitrogen ventilation of 4.2 L/h after the temperature of the catalyst layer was lowered to 340° C., the vaporized mixture of cyclohexanone oxime/methanol=1/1.8 (weight ratio) was supplied to the reaction tube at a supply rate of 8.4 g/h (WHSV of cyclohexanone oxime=8 $h^{-1}$) to perform reaction for 5.25 hours. The reaction gas was collected during each period of 0 to 0.25 hour and 5 to 5.25 hour after starting the reaction to show in Table 1 conversion of cyclohexanone oxime and selectivity of e-caprolactam calculated by analyzing with gas chromatography.

Example 1

26 g of USED CATALYST A obtained in Reference Example 1(a) was put in an eggplant-shaped flask, to which mixed liquid of 60 g of ethanol, 2.5 g of tetramethoxysilane and 2.0 g of water were added and stirred at room temperature for 3 hours. The solvent was distilled out of the mixture under normal pressure at a temperature of 90 to 120° C., and the mixture was thereafter dried. The obtained catalyst was put in an autoclave, to which mixed liquid (pH=11.5) of 110 g of 7.5% by weight-ammonium nitrate aqueous solution, 168 g of 25% by weight-ammonia aqueous solution and 0.039 g of tetra-n-propylammonium bromide was added and stirred at a temperature of 90° C. for 2 hours. The mixture was filtered and the residual solid through filtration was washed and dried to obtain a regenerated catalyst. The regenerated catalyst was evaluated in the same manner as Reference Example 1(b) to show the results in Table 1.

Example 2

26 g of USED CATALYST A obtained in Reference Example 1(a) was put in an eggplant-shaped flask, to which mixed liquid of 40 g of ethanol, 14 g of tetramethoxysilane and 8.0 g of water were added and stirred at room temperature for 3 hours. The solvent was distilled out of the mixture under normal pressure at a temperature of 90 to 120° C., and the mixture was thereafter dried. The obtained catalyst was put in an autoclave, to which mixed liquid (pH=11.5) of 110 g of 7.5% by weight-ammonium nitrate aqueous solution, 168 g of 25% by weight-ammonia aqueous solution and 0.039 g of tetra-n-propylammonium bromide were added and stirred at a temperature of 90° C. for 2 hours. The mixture was filtered and the residual solid through filtration was washed and dried to obtain a regenerated catalyst. The regenerated catalyst was evaluated in the same manner as Reference Example 1(b) to show the results in Table 1.

Example 3

18 g of USED CATALYST A obtained in Reference Example 1(a) was put in an eggplant-shaped flask, to which mixed liquid of 28 g of ethanol, 9.7 g of tetramethoxysilane and 6.0 g of water were added and stirred at room temperature for 3 hours. The solvent was distilled out of the mixture under normal pressure at a temperature of 90 to 120° C., and the mixture was thereafter dried. The obtained catalyst was put in an autoclave, to which mixed liquid (pH=11.5) of 77 g of 7.5% by weight-ammonium nitrate aqueous solution, 118 g of 25% by weight-ammonia aqueous solution and 0.7 g of 1.0% by weight of ethanol solution of tri-n-propylamine were added and stirred at a temperature of 90° C. for 2 hours. The mixture was filtered and the residual solid through filtration was washed and dried to obtain a regenerated catalyst. The regenerated catalyst was evaluated in the same manner as Reference Example 1(b) to show the results in Table 1.

Example 4

18 g of USED CATALYST B obtained in Reference Example 1(a) was put in an eggplant-shaped flask, to which mixed liquid of 28 g of ethanol, 1.2 g of tetraethoxysilane, 0.027 g of tetra-n-propylammonium bromide and 2.0 g of water were added and stirred at room temperature for 3 hours. The solvent was distilled out of the mixture under normal pressure at a temperature of 90 to 120° C., and the mixture was thereafter dried. The obtained catalyst was put in an autoclave, to which mixed liquid (pH=11.5) of 77 g of 7.5% by weight-ammonium nitrate aqueous solution, 118 g of 25% by weight-ammonia aqueous solution and 0.027 g of tetra-n-propylammonium bromide were added and stirred at a temperature of 90° C. for 4 hours. The mixture was filtered and the residual solid through filtration was washed and dried to obtain a regenerated catalyst. The regenerated catalyst was evaluated in the same manner as Reference Example 1(b) to show the results in Table 1.

Example 5

18 g of USED CATALYST B obtained in Reference Example 1(a) was put in an eggplant-shaped flask, to which mixed liquid of 28 g of ethanol, 1.2 g of tetraethoxysilane, 0.7 g of 1.0% by weight of ethanol solution of tri-n-propylamine and 2.0 g of water were added and stirred at room temperature for 3 hours. The solvent was distilled out of the mixture under normal pressure at a temperature of 90 to 120° C., and the mixture was thereafter dried. The obtained catalyst was put in an autoclave, to which mixed liquid (pH=11.5) of 77 g of 7.5% by weight-ammonium nitrate aqueous solution, 118 g of 25% by weight-ammonia aqueous solution and 0.7 g of 1.0% by weight of ethanol solution of tri-n-propylamine were added and stirred at a temperature of 90° C. for 4 hours. The mixture was filtered and the residual solid through filtration was washed and dried to obtain a regenerated catalyst. The regenerated catalyst was evaluated in the same manner as Reference Example 1(b) to show the results in Table 1.

Example 6

18 g of USED CATALYST C obtained in Reference Example 1(a) was put in an eggplant-shaped flask, to which mixed liquid of 28 g of ethanol, 1.2 g of tetraethoxysilane, 0.027 g of tetra-n-propylammonium bromide and 2.0 g of water were added and stirred at room temperature for 3 hours. The solvent was distilled out of the mixture under normal pressure at a temperature of 90 to 120° C., and the mixture was thereafter dried. The obtained catalyst was put in an autoclave, to which mixed liquid (pH=11.5) of 77 g of 7.5% by weight-ammonium nitrate aqueous solution, 118 g of 25% by weight-ammonia aqueous solution and 0.027 g of tetra-n-propylammonium bromide were added and stirred at a temperature of 90° C. for 4 hours. The mixture was filtered and the residual solid through filtration was washed and dried to obtain a regenerated catalyst. The regenerated catalyst was evaluated in the same manner as Reference Example 1(b) to show the results in Table 1.

Comparative Example 1

26 g of USED CATALYST A obtained in Reference Example 1(a) was put in an autoclave, to which mixed liquid (pH=11.5) of 110 g of 7.5% by weight-ammonium nitrate aqueous solution and 168 g of 25% by weight-ammonia aqueous solution were added and stirred at a temperature of 90° C. for 1 hour. The mixture was filtered and the residual solid through filtration was washed and dried to obtain a regenerated catalyst. The regenerated catalyst was evaluated in the same manner as Reference Example 1(b) to show the results in Table 1.

Comparative Example 2

26 g of USED CATALYST A obtained in Reference Example 1(a) was put in an autoclave, to which mixed liquid (pH=11.5) of 110 g of 7.5% by weight-ammonium nitrate aqueous solution, 168 g of 25% by weight-ammonia aqueous solution and 0.039 g of tetra-n-propylammonium bromide were added and stirred at a temperature of 90° C. for 2 hours. The mixture was filtered and the residual solid through filtration was washed and dried to obtain a regenerated catalyst.

The regenerated catalyst was evaluated in the same manner as Reference Example 1(b) to show the results in Table 1.

Comparative Example 3

26 g of USED CATALYST A obtained in Reference Example 1(a) was put in an eggplant-shaped flask, to which mixed liquid of 40 g of ethanol, 14 g of tetramethoxysilane and 8.0 g of water were added and stirred at room temperature for 3 hours. The solvent was distilled out of the mixture under normal pressure at a temperature of 90 to 120° C., and the mixture was thereafter dried. The catalyst on which the silicon compound was adsorbed was evaluated in the same manner as Reference Example 1(b) to show the results in Table 1.

TABLE 1

|  | 0~0.25 h | | 5~5.25 h | |
| --- | --- | --- | --- | --- |
|  | conversion (%) | selectivity (%) | conversion (%) | selectivity (%) |
| Reference Example 1 | 98.6 | 92.6 | 91.0 | 95.0 |
| Example 1 | 100 | 95.2 | 100 | 96.8 |
| Example 2 | 100 | 95.8 | 99.9 | 96.8 |
| Example 3 | 100 | 94.9 | 99.7 | 96.3 |
| Example 4 | 100 | 95.0 | 100 | 96.5 |
| Example 5 | 100 | 95.4 | 100 | 96.8 |
| Example 6 | 100 | 95.3 | 100 | 96.6 |
| Comparative Example 1 | 100 | 94.5 | 99.9 | 96.0 |
| Comparative Example 2 | 100 | 94.9 | 100 | 96.5 |
| Comparative Example 3 | 86.7 | 92.7 | 58.0 | 94.6 |

What is claimed is:

1. A process for regenerating a catalyst for producing e-caprolactam comprising the steps of adsorbing a silicon compound on a zeolite catalyst that had been used for a Beckmann rearrangement reaction of cyclohexanone oxime and contacting the catalyst with an aqueous solution containing a compound selected from a quaternary ammonium compound, a lower alkylamine and ammonia.

2. The process according to claim 1, wherein the aqueous solution contains ammonia and a compound selected from a quaternary ammonium compound and a lower alkylamine.

3. The process according to claim 1, wherein the silicon compound is adsorbed on the zeolite catalyst and thereafter the catalyst is contacted with the aqueous solution.

4. The process according to claim 2, wherein the silicon compound is adsorbed on the zeolite catalyst and thereafter the catalyst is contacted with the aqueous solution.

5. A process for producing e-caprolactam comprising subjecting cyclohexanone oxime to a Beckmann rearrangement reaction in the presence of a catalyst for producing e-caprolactam which is regenerated by the process according to claim 1.

* * * * *